(12) United States Patent
Neumann

(10) Patent No.: US 11,437,147 B2
(45) Date of Patent: Sep. 6, 2022

(54) METHOD AND SYSTEMS FOR SIMULATING A VITALITY METRIC

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 0 days.

(21) Appl. No.: 17/007,269

(22) Filed: Aug. 31, 2020

(65) Prior Publication Data

US 2022/0068486 A1 Mar. 3, 2022

(51) Int. Cl.
*G16H 50/30* (2018.01)
*G16H 20/30* (2018.01)
(Continued)

(52) U.S. Cl.
CPC ........... *G16H 50/30* (2018.01); *G06N 20/00* (2019.01); *G16H 20/30* (2018.01); *G16H 50/20* (2018.01)

(58) Field of Classification Search
None
See application file for complete search history.

(56) References Cited

U.S. PATENT DOCUMENTS 6,980,999 B1 12/2005 Grana
8,920,175 B2 12/2014 Black et al.
(Continued)

FOREIGN PATENT DOCUMENTS

WO WO-2011082421 A * 7/2011 ............... G16B 5/00
WO WO-2015023674 A1 * 2/2015 ............. G16H 50/30
(Continued)

OTHER PUBLICATIONS

Zhao et al., Physical activity recommendation for exergame player modeling using Machine Learning Approach, 2020 IEEE 8th International Conference on Serious Games and Applications for Health (SEGAH) (2020), https://ieeexplore.ieee.org/stamp/stamp.jsp?tp=&arnumber=9201820 (last visited Apr. 15, 2022). (Year: 2020).*
(Continued)

*Primary Examiner* — John P Go
*Assistant Examiner* — Nicholas Akogyeram, II
(74) *Attorney, Agent, or Firm* — Caldwell Intellectual Property Law

(57) ABSTRACT

A system for simulating a vitality metric, the system comprising a computing device, wherein the computing device is configured to retrieve, from a user, a biotic extraction, generate a vitality metric, using a machine-learning model, wherein generating a vitality metric further comprises training a machine-learning model with training data corresponding to measuring biotic parameters present in the biotic extraction data and determining a metric that is a summation of all individual biotic parameters present in the biotic extraction data. Computing device determines a simulated metric, using a simulation machine-learning process, wherein the simulation perturbs a biotic parameter present in the vitality metric, wherein a biotic parameter is an element of numerical data relating to an element of data present in the at least a user biotic extraction. Computing device provides, to a user, a vitality metric and at least a user effort that resulted in a simulated metric.

18 Claims, 7 Drawing Sheets

(51) Int. Cl.
  *G06N 20/00* (2019.01)
  *G16H 50/20* (2018.01)

(56) References Cited

U.S. PATENT DOCUMENTS

| | | | |
|---|---|---|---|
| 10,360,495 B2 | 7/2019 | Chapela et al. | |
| 11,037,669 B2* | 6/2021 | Solari | G16H 20/60 |
| 2006/0272652 A1* | 12/2006 | Stocker | G16H 50/50 |
| | | | 128/898 |
| 2014/0255882 A1 | 9/2014 | Hadad et al. | |
| 2015/0161910 A1 | 6/2015 | Bailor | |
| 2016/0364548 A1 | 12/2016 | Springer | |
| 2017/0124269 A1* | 5/2017 | McNair | G16H 50/20 |
| 2017/0300655 A1* | 10/2017 | Lane | G16H 10/60 |
| 2018/0144820 A1 | 5/2018 | Grimmer et al. | |
| 2018/0165418 A1* | 6/2018 | Swartz | G16H 50/70 |
| 2018/0211723 A1* | 7/2018 | Coles | G16H 20/60 |
| 2018/0233064 A1 | 8/2018 | Dunn et al. | |
| 2018/0233223 A1* | 8/2018 | Solari | G16H 20/60 |
| 2018/0271379 A1* | 9/2018 | Watanabe | A61B 5/01 |
| 2018/0293638 A1 | 10/2018 | Simpson | |
| 2018/0315499 A1* | 11/2018 | Appelbaum | G16H 20/30 |
| 2019/0333614 A1* | 10/2019 | Burger | G16H 50/70 |
| 2020/0138360 A1* | 5/2020 | Fan | A61B 5/14551 |
| 2020/0193326 A1* | 6/2020 | Leabman | G01S 13/87 |

FOREIGN PATENT DOCUMENTS

| | | |
|---|---|---|
| WO | WO2016065463 | 5/2016 |
| WO | WO2020115362 | 6/2020 |

OTHER PUBLICATIONS https://www.ncbi.nlm.nih.gov/pmc/articles/PMC5579706/pdf/nutrients-09-00913.pdf.
https://www.researchgate.net/publication/334529528_A_food_recommender_system_considering_nutritional_information_and_user_preferences (via 'Download full-text PDF' link).
https://www.researchgate.net/profile/Luis_Rita2/publication/340133854_Machine_Learning_for_Building_a_Food_Recommendation_System/links/5e7aa059a6fdcc57b7bbaf10/Machine-Learning-for-Building-a-Food-Recommendation-System.pdf.

* cited by examiner

METHOD AND SYSTEMS FOR SIMULATING A VITALITY METRIC

FIELD OF THE INVENTION

The present invention generally relates to the field of machine-learning. In particular, the present invention is directed to a method and system for simulating a vitality metric.

BACKGROUND

Accurate and efficient methods of calculation of user-friendly physiological metrics using machine-learning is largely unknown due to the nature of the large, variable datasets provided by users. Furthermore, providing clear and concise metrics and accurate instructions to improve these metrics is difficult.

SUMMARY OF THE DISCLOSURE

In an aspect, a system for simulating a vitality metric, the system including a computing device, wherein the computing device is designed and configured to retrieve a biotic extraction pertaining to a user, generate a first vitality metric using a metric machine-learning model and the biotic extraction, wherein generating the first vitality metric includes training a metric machine-learning model with training data, the training data containing a plurality of data entries correlating biotic extraction data to measured biotic parameters, generating the first vitality metric, the first vitality metric containing a summation of all individual biotic parameters associated with the biotic extraction data, as a function of the metric machine-learning model, determine a simulated metric as a function of the generated first vitality metric of a user, wherein determining the simulated metric includes perturbing a biotic parameter present in the first vitality metric, and provide, to a user, the first vitality metric and at least a user effort that produces the simulated metric.

In another aspect, a method for simulating a vitality metric, the method including retrieving, by a computing device, a biotic extraction pertaining to a user, generating, by the computing device, a first vitality metric using a metric machine-learning model and the biotic extraction, wherein generating the first vitality metric includes training a metric machine-learning model with training data, the training data containing a plurality of data entries correlating biotic extraction data to measured biotic parameters, generating the first vitality metric, the first vitality metric containing a summation of all individual biotic parameters associated with the biotic extraction data, as a function of the metric machine-learning model, determining, by the computing device, a simulated metric as a function of the generated first vitality metric of a user, wherein determining the simulated metric includes perturbing a biotic parameter present in the first vitality metric, and providing, by the computing device, to a user, the first vitality metric and at least a user effort that produces the simulated metric.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for simulating vitality metrics. In an embodiment, the system may include a computing device configured to receive biotic extraction data of a user, including data including information regarding how a user interaction with its ecological environment. In an embodiment, computing device may use machine-learning models to map the user biotic extraction data to a vitality metric. In an embodiment, computing device may simulate a plurality of vitality metric as a function of user actions using a simulation machine-learning process and determine what actions a user may perform to improve the vitality score. A computing device may provide to a user, at least a user effort that results, for instance and without limitation, in an increase of vitality metric. In an embodiment, a user may select efforts that result in an increased vitality metric, as determined by the simulation algorithm, and the computing device may guide a user to a destination for performing the effort. Computing device may update a vitality metric as a function of the user effort.

Figure 1:
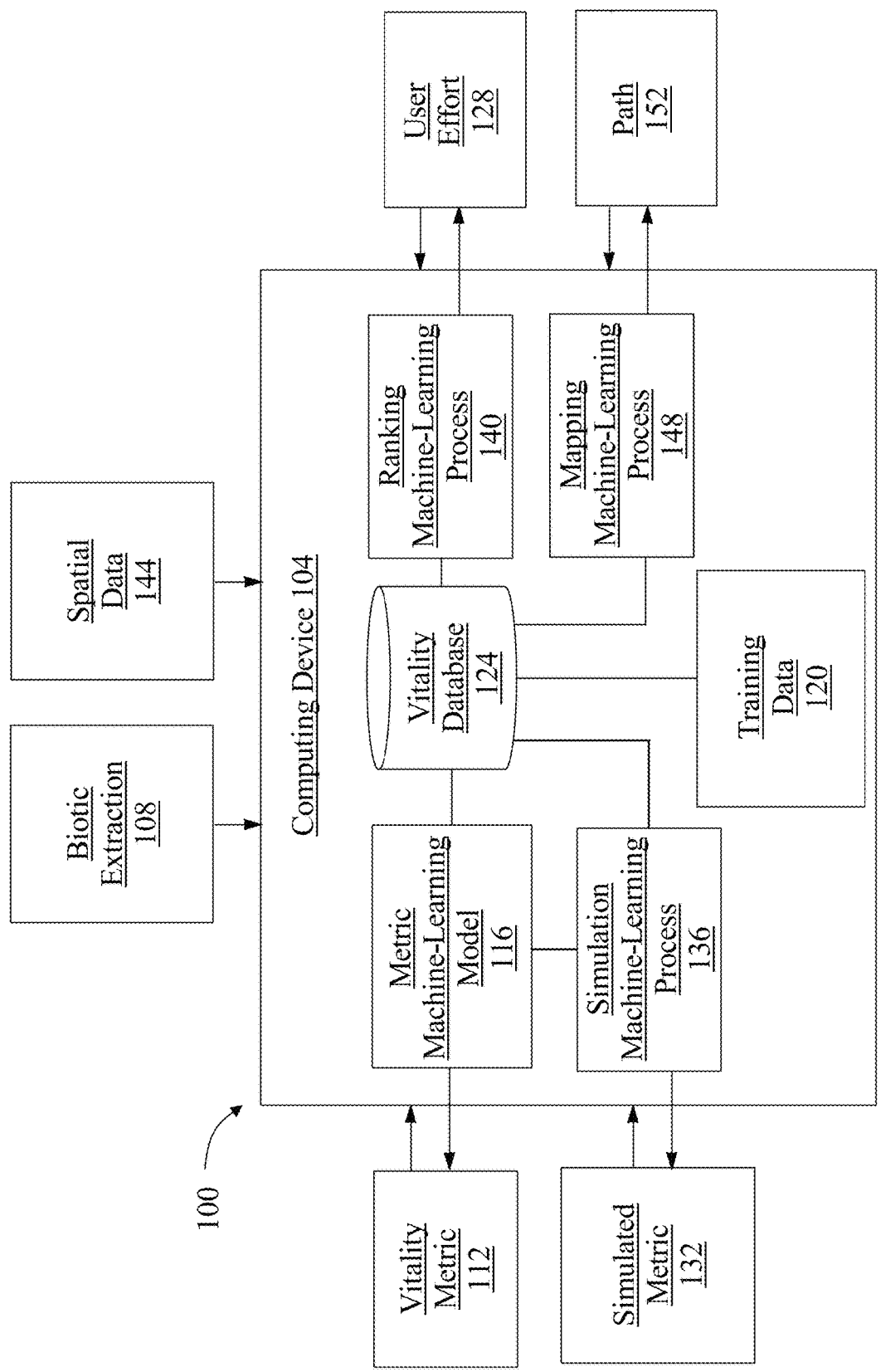
FIG. 1 is a block diagram of an exemplary embodiment of a system of simulating a vitality metric.

Referring now to FIG. 1, an exemplary embodiment of a system 100 for simulating a vitality metric is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 may retrieve, from a user, a biotic extraction 108. As used in this disclosure, "retrieve" from a user means accepting, collecting, or otherwise receiving input from a user and/or device. A "biotic extraction," as used in this disclosure, is data that relates to a user's health and physiology, including chemical, biological, physical, and behavioral data relating to a user, and how a user relates to their natural, social, and built environments. In non-limiting illustrative examples, a biotic extraction may be a combination of a user's health data including medical history, user diet, exercise, sleep, data corresponding to timestamps and geographical locations for how a user spends his or her time, data regarding how a user spends money, user social media information, and the like.

With continued reference to FIG. 1, biotic extraction may include wearable device data that tracks how a user relates with his or her environments. Wearable device data may include data and associated analysis corresponding to, for instance and without limitation, accelerometer data, pedometer data, gyroscope data, electrocardiography (ECG) data, electrooculography (EOG) data, bioimpedance data, blood pressure and heart rate monitoring, oxygenation data, biosensors, fitness trackers, force monitors, motion sensors, video and voice capture data, social media platform data, and the like. Biotic extraction data may be provided by a user, a second individual on behalf of a user, for instance and without limitation a physician, medical professional, nurse, hospice care worker, mental health professional, and the like. Biotic extraction data may originate from a user questionnaire, graphical user interface (GUI), or any other suitable forum for gathering information regarding biotic extraction. Persons skilled in the art, upon review of this disclosure in its entirety, will be aware of the various ways in which biotic data may be collected and provided to the system described herein.

Continuing in reference to FIG. 1, computing device 104 may generate a vitality metric using a metric machine-learning model and the biotic extraction 108, wherein generating a vitality metric may include training a metric machine-learning model with training data corresponding to measuring biotic parameters present in the biotic extraction 108 data, and determining a metric that is a summation of all individual biotic parameters present in the biotic extraction 108 data. A "biotic parameter," as used in this disclosure, is a variable element of data relating to an element present in the at least a user biotic extraction. Biotic parameters may be qualitative elements such as binary elements, for instance and without limitation a Boolean, 'yes' or 'no', 'true' or 'false', a category name, identifier, or that like, that may apply to an element of biotic extraction 108. In non-limiting illustrative examples, a biotic parameter may include qualitative elements such as the presence or absence of exercise, names of the types of activities as part of exercise, and the like. Biotic parameters may be quantitative elements represented, for instance and without limitation, as numerical values, polar coordinates, functions, matrices, and the like. In non-limiting illustrative examples, a biotic parameter may include quantitative elements such as used to describe frequency, duration, and intensity of exercise, number of repetitions, and the like.

Still referring to FIG. 1, a "vitality metric," as used in this disclosure is a singular numerical value that summarizes a plurality of biotic parameters, wherein the numerical value relates to a user's overall health, energy, and well-being, as can be determined from biotic extraction 108 data. In non-limiting illustrative examples, a vitality metric 112 may be a numerical value that summarizes a user's health, energy, and well-being as it relates to current nutrition, sleep deprivation, exercise frequency, body mass index (BMI), time spent working, time spend pursuing leisure activity, number of friends, acquaintances, and family members, aptitude battery, financial security, mental health, and the like. A metric machine-learning model 116 may locate discrete biotic parameters present in the biotic extraction 108 data which can be assigned numerical values based on training data 120, for instance and without limitation, a numerical value which is a score of how 'fit' a user may be based on a variety of fitness categories. A computing device may determine a vitality metric 112 by using a mathematical operation, such as addition, to obtain a final metric which corresponds to all categories which can be assigned numerical values using the machine-learning model. There may be ranges of numerical values that can be applied to each parameter, for instance and without limitation, as can be simulated from an input parameter, ranges of values determined from training, and the like, as described in further detail below.

Figure 2:
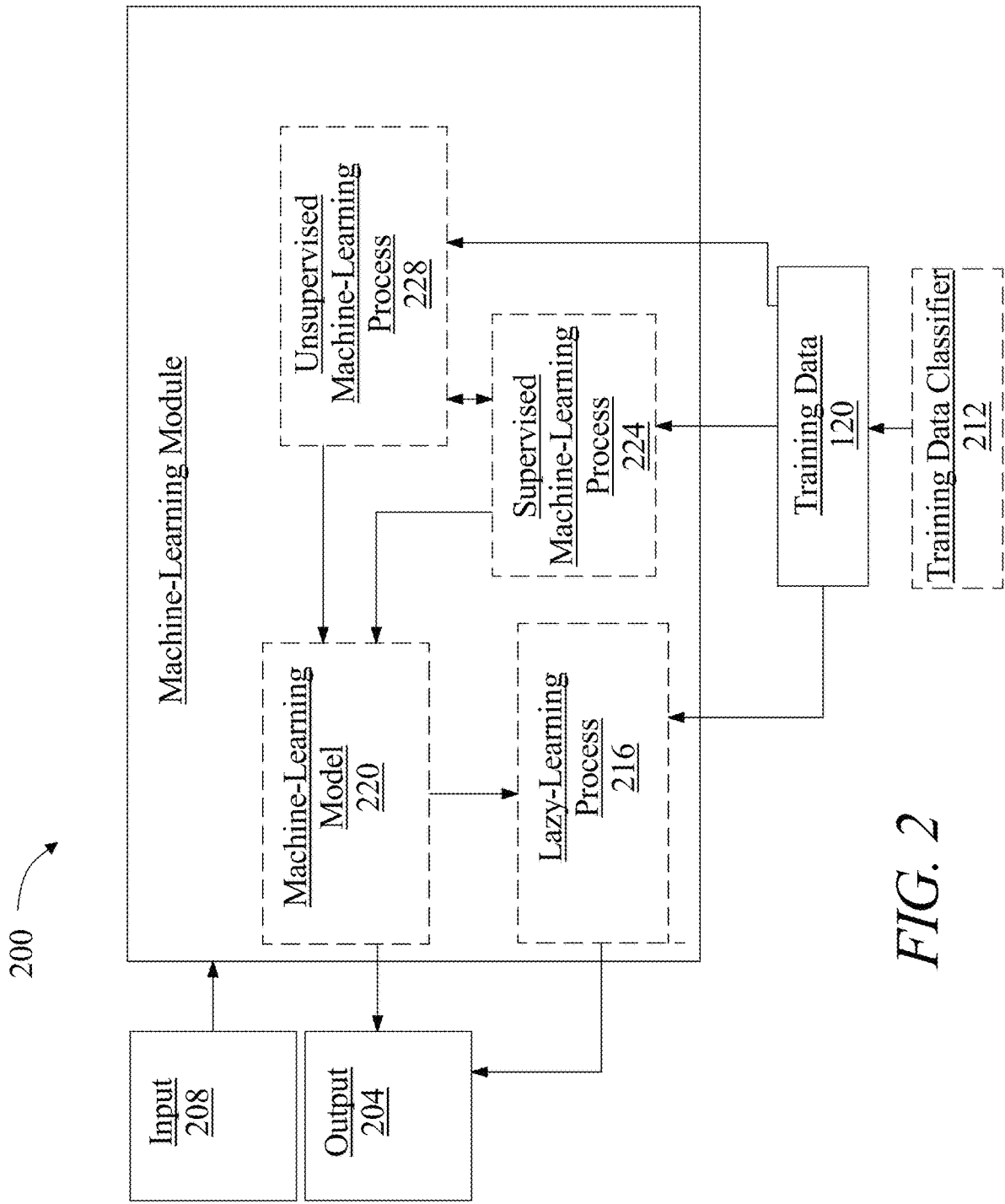
FIG. 2 is a block diagram of an exemplary embodiment of a machine-learning module.

Referring now to FIG. 2 an exemplary embodiment of a machine-learning module 200 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 120 to generate an algorithm that will be performed by a computing device/module to produce outputs 204 given data provided as inputs 208; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 120 may include a plurality of data entries, each entry representing a set of data elements that were recorded, received, and/or generated together; data elements may be correlated by shared existence in a given data entry, by proximity in a given data entry, or the like. Training data 120 may correspond to at least an element of data entry that may be used for training, a subset of a training data 120, and/or multiple training data sets 204. Multiple data entries in training data 120 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 120 according to various correlations; correlations may indicate causative and/or predictive links between categories of data elements, which may be modeled as relationships such as mathematical relationships by machine-learning processes as described in further detail below. Training data 120 may be formatted and/or organized by categories of data elements, for instance by associating data elements with one or more descriptors corresponding to categories of data elements. As a non-limiting example, training data 120 may include data entered in standardized forms by persons or processes, such that entry of a given data element in a given field in a form may be mapped to one or more descriptors of categories. Elements in training data 120 may be linked to descriptors of categories by tags, tokens, or other data elements; for instance, and without limitation, training data 120 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 120 may include one or more elements that are not categorized; that is, training data 120 may not be formatted or contain descriptors for some elements of data. Machine-learning algorithms and/or other processes may sort training data 120 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 120 to be made applicable for two or more distinct machine-learning algorithms as described in further detail below. Training data 120 used by machine-learning module 200 may correlate any input data as described in this disclosure to any output data as described in this disclosure. As a non-limiting illustrative example biotic extraction 108 input data and vitality metrics 112 outputs determined from training data that relates biotic extraction 108 data to ranges of numerical values that may be used as vitality metrics 112.

Further referring to FIG. 2, training data may be filtered, sorted, and/or selected using one or more supervised and/or unsupervised machine-learning processes and/or models as described in further detail below; such models may include without limitation a training data classifier 212. Training data classifier 212 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 120. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 212 may classify elements of training data to sections of biotic extraction 108 data as it relates to subsets of users and the corresponding numerical values that result in the vitality metric 112.

Still referring to FIG. 2, machine-learning module 200 may be configured to perform a lazy-learning process 216 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 120. Heuristic may include selecting some number of highest-ranking associations and/or training data 120 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning model 220. A "machine-learning model 220," as used in this disclosure, is a mathematical and/or algorithmic representation of a relationship between inputs and outputs, as generated using any machine-learning process including without limitation any process as described above, and stored in memory; an input is submitted to a machine-learning model 220 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 220 may be generated by creating an artificial neural network, such as a convolutional neural network comprising an input layer of nodes, one or more intermediate layers, and an output layer of nodes. Connections between nodes may be created via the process of "training" the network, in which elements from a training data 120 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 224. At least a supervised machine-learning process 224, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include biotic extraction 108 data, as described above, as inputs, vitality metrics 112 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 120. Persons skilled in the art, upon reviewing the entirety of this disclosure, will be aware of various possible variations of at least a supervised machine-learning process 224 that may be used to determine relation between inputs and outputs. Supervised machine-learning processes may include classification algorithms as defined above.

Further referring to FIG. 2, machine learning processes may include at least an unsupervised machine-learning processes 228. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 220 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic, or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 120 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 120.

Referring back now to FIG. 1, computing device 104 generating a vitality metric 112 may include calculating a numerical metric for biotic parameters in the biotic extraction by using the metric machine-learning model 116. In non-limiting illustrative examples, metric machine-learning model 116 may determine the numerical value using data stored and/or retrieved, for instance and without limitation, a vitality database 124, an online research repository, social media platform, expert submission, mobile lifestyle application, or the like, as described in further detail below.

Figure 3:
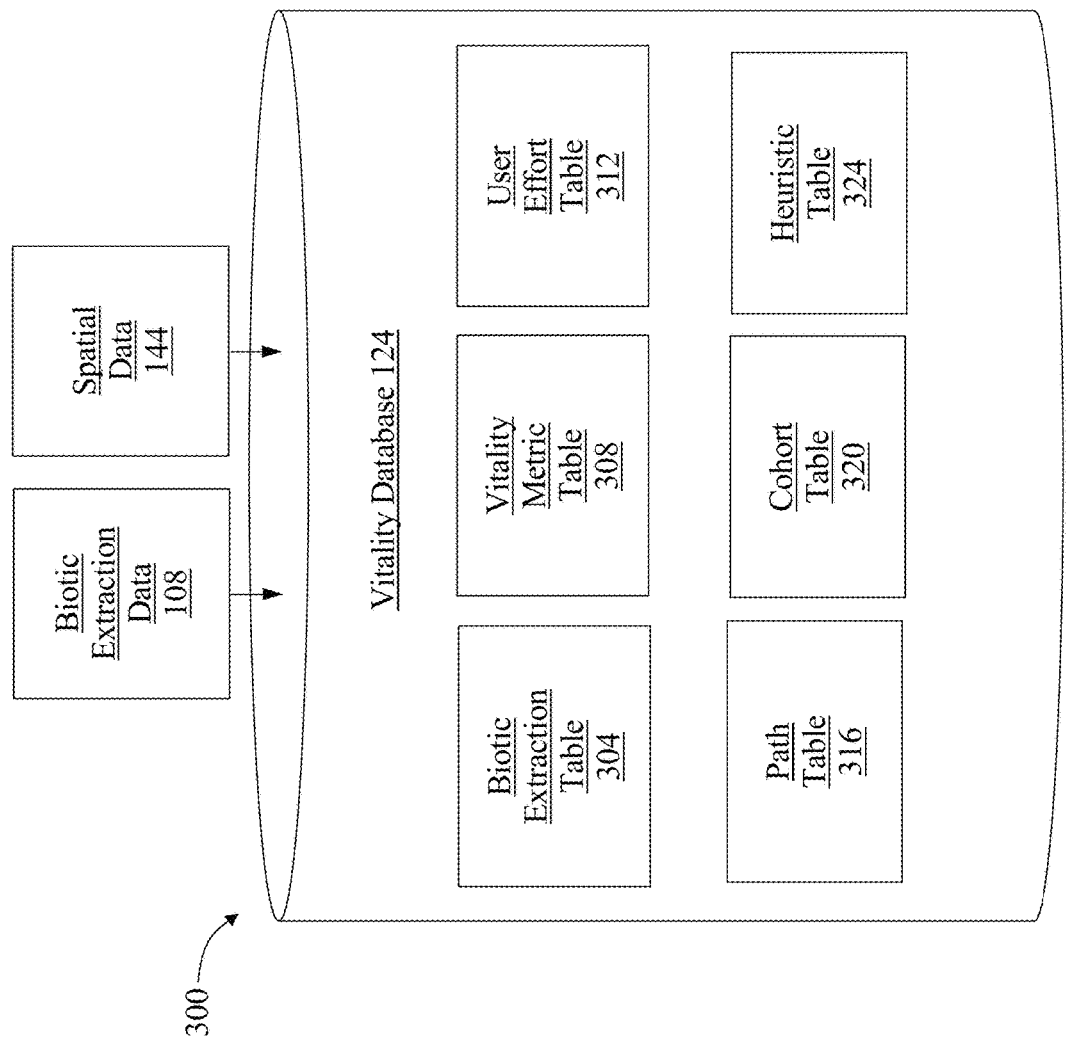
FIG. 3 is a block diagram of an exemplary embodiment of a vitality database.

Referring now to FIG. 3, a non-limiting exemplary embodiment 300 of a vitality database 124 is illustrated. Vitality database 124 may be implemented, without limitation, as a relational database, a key-value retrieval database such as a NOSQL database, or any other format or structure for use as a database that a person skilled in the art would recognize as suitable upon review of the entirety of this disclosure. Vitality database 124 may alternatively or additionally be implemented using a distributed data storage protocol and/or data structure, such as a distributed hash table and the like. Vitality database 124 may include a plurality of data entries and/or records, as described above. Data entries in a vitality database 124 may be flagged with or linked to one or more additional elements of information, which may be reflected in data entry cells and/or in linked tables such as tables related by one or more indices in a relational database. Vitality database 124 may be designated as an online repository of data, or other network-integrated data repository. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 3, vitality database 124 may include, without limitation, a biotic extraction table 304, vitality metric table 308, user action table 312, path table 316, cohort table 320, and/or heuristic table 324. Determinations by a machine-learning process, machine-learning model, and/or scoring function may also be stored and/or retrieved from the vitality database 124, for instance in non-limiting examples a classifier describing a subset of users with alike biological extraction data as it relates to biological degradation rates. Determinations by a machine-learning model, for instance for calculating a degradation rate and/or a machine-learning process for determining an antidote strategy, may also be stored and/or retrieved from the vitality database 124. As a non-limiting example, vitality database 124 may organize data according to one or more instruction tables. One or more vitality database 124 tables may be linked to one another by, for instance in a non-limiting example, common column values. For instance, a common column between two tables of vitality database 124 may include an identifier of a submission, such as a form entry, textual submission, degradation rates, and the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, and the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of a vitality database 124 may include, as a non-limiting example, a biotic extraction table 304, which may include elements of user biotic extraction 108 data, as described above, and any associated data relating to wearable device data, determinations made by an expert, medical professional, physical trainer, or the like, including medical history data, physiological measurements, mental health, medical conditions, diagnoses, diseases, or any other factors for use in determining vitality metrics 112, simulated parameters, user efforts, and/or other elements of data computing device 104 and/or system 100 may store, retrieve, and use to determine usefulness and/or relevance of biotic extraction 108 data in determining vitality metrics 112, simulated parameters, and/or user efforts as described in this disclosure. One or more tables may include vitality metric table 308, which may include numerical values, functions, vectors, matrices, coordinates, graphical data, parameters, and the like, for instance and without limitation, that link user biotic extraction 108 to ranges of the above. Vitality metric table 308 may include simulated parameters related to calculating a vitality metric and associated biotic extraction 108 data. One or more tables may include a user effort table 312, which may correlate user efforts, actions, or other tasks that a user may perform to influence a vitality metric as it pertains to a determination about vitality metric 112, simulated parameter, user effort, path, and the like, including any outcomes, models, heuristics, scores and/or combinations thereof as they may correspond to rankings, determination, calculations, or combinations of items listed as numerical values, metrics, functions, vectors, matrices, and the like, that corresponds to determining a vitality metric 112. One or more tables may include, without limitation, a path table 316 which may contain one or more inputs identifying one or more categories of data, for instance locations to fitness centers, gyms, mental health professionals, clinics, hospitals, health food stores, libraries, and the like. Path table 316 may contain and organize elements of spaciotemporal data such as geographical destinations, locations, global positioning system (GPS) coordinates, and the like, of where a user is located and/or nearby locations that may be prescribed to a user for performing a user effort. One or more tables may include, without limitation, a cohort category table 320 which may contain one or more inputs identifying one or more categories of data, for instance demographic data, lifestyle data, physiological data, sleep pattern data, or the like, with regard to which users having matching or similar data may be expected to have similar vitality metrics 112, social media contacts, and/or user actions as a result of a machine-learning process determination, simulation algorithm, ranking algorithm output elements and/or other data input elements. One or more tables may include, without limitation, a heuristic table 324, which may include one or more inputs describing potential mathematical relationships between at least an element of user data and, for instance and without limitation, biotic extraction 108 data, vitality metrics 112, simulated parameters, and/or user actions as a result of a machine-learning process determination, simulation outputs, and rankings thereof, and how they may change as a function of a user effort, as described in further detail below.

Referring back now to FIG. 1, vitality metric 112 may be determined as a function of at least a user effort 128, wherein a vitality metric 112 is provided periodically to a user as a function of the user efforts 128. A "user effort," as used in this disclosure, is a user act, measure, activity, movement, work, or the like, that a user participates in or performs to influence a vitality metric 112. A vitality metric 112 may be periodically updated as a function of a user effort 128. Periodically may refer to any sampling of time. In non-limiting illustrative examples, a vitality metric 112 may be updated and recalculated using a metric machine-learning model 116 iteratively as soon as an identified user action 128 is performed. In further non-limiting illustrative examples, a vitality metric 112 may be stored and/or retrieved alongside a series of simulated parameters which are theoretical and/or expected vitality metrics 112 according to user efforts 128, wherein as soon as a user effort 128 is performed, the magnitude, amount, time, or degree to which the user action 128 was performed can be used to adjust, modify, or otherwise recalculate the vitality metric 112 in predetermined increments. In such an example, this may be done to periodically provide an accurate vitality metric 112, wherein periodic may refer to instantaneous updates to the vitality metric 112.

Continuing in reference to FIG. 1, computing device 104 may determine a simulated metric 132, using a simulation machine-learning process 136 and a generated vitality metric 112 of a user, wherein determining a simulated metric 132 may include generating a simulation machine-learning process 136, wherein the simulation machine-learning process 136 perturbs a biotic parameter present in the vitality metric 112, wherein a biotic parameter is a variable element of data relating to an element present in the at least a user biotic extraction 108. A "biotic parameter," as used in this disclosure, is an element of data described as a quantitative variable, such as a numerical value, and/or an element of data described by a qualitative variable such as a Boolean data type (true/false, yes/no), a category, and the like, relating to a biotic extraction 108 datum. As used in this disclosure, "perturbing" a parameter is selecting at least a value of a parameter, where the at least a value of the parameter is sampled from and/or through a range of values, instances, or the like, either in a random and/or guided manner; for instance, perturbing may include selecting and/or inputting a plurality of values for the parameter. Perturbing a parameter may include selecting a 'stand-in' value for that parameter, wherein the stand-in value may take the place of an original value. The perturbed value may be a quantitative value, such as a numerical value, selected randomly, for instance as in selecting any value within a finite range wherein the value is selected with equal probability of selecting any of the values. Alternatively or additionally, perturbing parameters may include selecting values in a guided manner, for instance such as in starting with a value and moving in whole number increments in an increasing manner. The perturbed value may be a qualitative value such as a discrete category such as 'exercise', a type such as 'swimming', or the like, that may be selected among a range of discrete categories.

For instance in non-limiting illustrative examples, a biotic parameter perturbed by a simulation machine-learning process 136 in generating an output may be quantitative parameters of lengths of time of exercise combined with qualitative categories of exercise such as biking, swimming, weightlifting, etc. In such an example, a simulation machine-learning process 136 may generate a simulated metric 132 for varying lengths of time of exercise, in varying increments of time, for each category of exercise. A "simulated metric," as used in this disclosure, is an output describing a vitality metric as a direct result of perturbing a parameter that can be affected by a user effort 128. In non-limiting illustrative examples, a simulated metric 132 may be an output describing a vitality metric 112 after applying various user efforts 128, such as choosing to exercise, alter sleep patterns, alter diet patterns, seek and maintain counseling, and the like.

With continued reference to FIG. 1, a simulation machine-learning process 136 used to generate a simulated metric 132 may be any computational algorithm, method, or the like, that may generate an output, of a plurality of outputs, given a range of input values that the simulation algorithm may select—in a random and/or guided manner—to provide a plurality of observations, outputs, or the like, wherein the nature of the outputs is not entirely known. Simulation machine-learning process 136 may be a stochastic simulation process such as Markov Model Monte Carlo (MMMC) simulations, McKean-Vlasov processes, Monte Carlo localization, stochastic tunneling, among other probabilistic stochastic heuristics that randomly select numerical parameters from within a defined set of parameters and calculate an outcome for all selected parameters. Simulation machine-learning process 136 may be a probabilistic technique for approximating global optimum of a given function, matrix, vector space, or the like, such as simulated annealing algorithm, interacting Metropolis-Hasting algorithms, quantum annealing, Tabu search, Dual-phase evolution, reactive search optimization, and the like.

With continued reference to FIG. 1, simulation machine-learning process 136 may perform a computational simulation by randomly perturbing parameters, such as user efforts, biotic parameters, and the like, and determine the effect on a vitality metric 112, to determine which parameters result in an outcome that may be the same or different than a first input vitality metric 112. Simulation machine-learning process 136 may calculate the output for a simulated metric 132 for all values within a range of values corresponding to a parameter in the biotic extraction 108 data; alternatively or additionally simulation algorithm may generate a simulated metric 132 for values of parameters outside of the biotic extraction 108 data that was originally retrieved by computing device 108. For instance in non-limiting illustrative examples, a simulation machine-learning process 136 may calculate a simulated metric 132 for all values of exercise, wherein user efforts are time amounts in 1-minute increments over weekly periods. In such an example, a user vitality metric 112 may increase with daily exercise for certain efforts such as running, biking, hiking, swimming, weightlifting, and the like, wherein values above 3-hour daily exercise result in sharp decreases in vitality metric 112 over several consecutive days, wherein values at 0.5-2 hour daily exercise increase vitality metric 112 over several consecutive weeks. Such a simulation may find that, with all other biotic extraction 108 data held constant, that maximal increase in vitality metric 112 was given specifically for running, biking, or swimming at 1-1.25 hour daily exercise over at least the next 7 consecutive days, given between 1-2 days of not exercising for every 5 days. A simulation machine-learning process 136 performed by a computing device 104 may retrieve, for instance from a vitality database 124, the metric machine-learning model 112, or any similar machine-learning model trained as descried above, to accurately and quickly determine how each parameters selected of the range of parameters may influence a vitality metric 112. In such an example, simulation machine-learning process 136 may then generate a large dataset of simulated metrics 132 based on what a user may hypothetical do; these data may be stored and/or retrieved from a vitality database 124 to more quickly update a user vitality metric 112 in the event they perform user efforts that resemble what was observed in the simulation.

With continued reference to FIG. 1, in non-limiting illustrative examples, a simulation machine-learning process 136 may be a Monte Carlo algorithm, or similar simulation algorithm as described above. A Monte Carlo simulation is a mathematical technique that may generate variables, numerical values, and the like, for modeling risk, outcomes, uncertainty, etc., of a certain system using a stochastic simulation process. Monte Carlo simulations may encompass a range of algorithms and mathematical analysis techniques such as A Monte Carlo simulation may generate a series of numerical values represented by traces, curves, functions, and the like, wherein each function may represent a sufficiently good solution and/or outcome to an optimization problem, wherein the solution may be represented by a polar coordinate, vector, function, or the like, that represents, for instance and without limitation, how a vitality metric 112 improves from implementing a user effort, wherein the order, magnitude, timing, and the like, of the user effort may be perturbed for each simulation. Each generated simulated metric 132 may have an associated parameter, wherein each parameter from a simulation may have associated with it a user effort, time amount, biotic extraction 108 element, or the like. Persons skilled in the art, upon review of this disclosure in its entirety, will be aware of the various simulation algorithms that may be performed by a processor to sample parameters associated with a medical treatment and calculate an associated prognosis value.

Continuing in reference to FIG. 1, computing device 104 determining a simulated metric 132 of a user may include generating a simulated vitality metric 112, using a first vitality metric 112 of a user as an input and a simulation machine-learning process 136, wherein the simulation machine-learning process 136 generates a simulated metric 132 corresponding to a numerical output, wherein the simulated metric 132 is a vitality metric 112 after applying a user effort, and providing, to a user, at least a simulated vitality metric 112 as a function of a plurality of user efforts. Simulation machine-learning process 136 may accept an input of a first vitality metric 112 of a user as a simulation 'seed', wherein the initial vitality metric 112 and associated data exists as a reference metric that a simulation may apply user efforts 128 to generate an output of a simulated metric 132. Computing device 104 may then provide to a user a simulated metric 112, of a plurality of simulated metrics 112, and at least an accompanying user effort 128, of a plurality of user efforts 128, that had an effect on a first vitality metric 112 to generate a simulated metric 112. In a non-limiting exemplary embodiment, providing user efforts 128 to a user and the associated effects of the efforts in the form of simulated metrics 112 may inform a user to pursue or otherwise select user efforts 128, wherein selecting a user effort 128 may provide a user with additional information to perform the user effort 128. This may allow a user to have a desired effect on their vitality metric 112.

Continuing in reference to FIG. 1, computing device 104 determining a simulated metric 132 may include identifying, as a function of the simulation machine-learning process 136 output, parameters that result in a simulated metric 132 that represent an improved vitality metric 112. Computing device 104 may identify a simulated metric 132 representing an improved vitality metric 112 by calculating a numerical difference by performing a mathematical operation, for instance and without limitation subtraction, between a vitality metric 112 and a simulated metric 132 to determine if a simulated metric 132 represents an improved metric. Computing device 104 may then identify the parameters the simulation machine-learning process 136 selected to result in the simulated metric 132 that represents a potential improved metric. In non-limiting illustrative examples, the simulation parameters may relate to user efforts 128, such as increased vitamin and nutrient intake, wherein increased vitamin and nutrient intake may be achieved by eating more leafy green vegetables.

Continuing in reference to FIG. 1, computing device 104 simulating a vitality metric 112 may include ranking, using a ranking machine-learning process 140, user efforts 128 as a function of the numerical change of the vitality metric 112. Computing device 104 may identify simulated metrics 132 and the associated user efforts 128 that represent improved vitality metrics 112, as described above, and rank the user efforts 128 using a ranking machine-learning process 140. A ranking machine-learning process may be a machine-learning algorithm, such as a supervised machine-learning algorithm, as described above, which may rank elements based on some criteria. A ranking algorithm may be any algorithm, as described above, for classification, wherein classification may be performed as a ranking of inputs to generate outputs classified into a ranked list, provided a criterion for ranking. In non-limiting illustrative examples, the ranking may be a limitation logistic regression and/or naïve Bayes ranking algorithm, nearest neighbor algorithm such as k-nearest neighbors, support vector machines, least squares support vector machines, fisher's linear discriminant, quadratic classifiers, decision trees, boosted trees, random forest classifiers, learning vector quantization, and/or neural network-based algorithms, as described above. In non-limiting illustrative examples, ranking criteria used by a ranking machine-learning process 140 for ranking user efforts 128 may include ranking based on magnitude of impact on a vitality metric 112. In such an example, user efforts 128 that resulted in an increased vitality metric 112 may be ranked based upon the magnitude of their effect on increasing a vitality metric 112. Alternatively or additionally. User efforts 128 may be ranked as a function of their addressability, difficulty of user, and the like, according to a user's environment, and the like.

Figure 4:
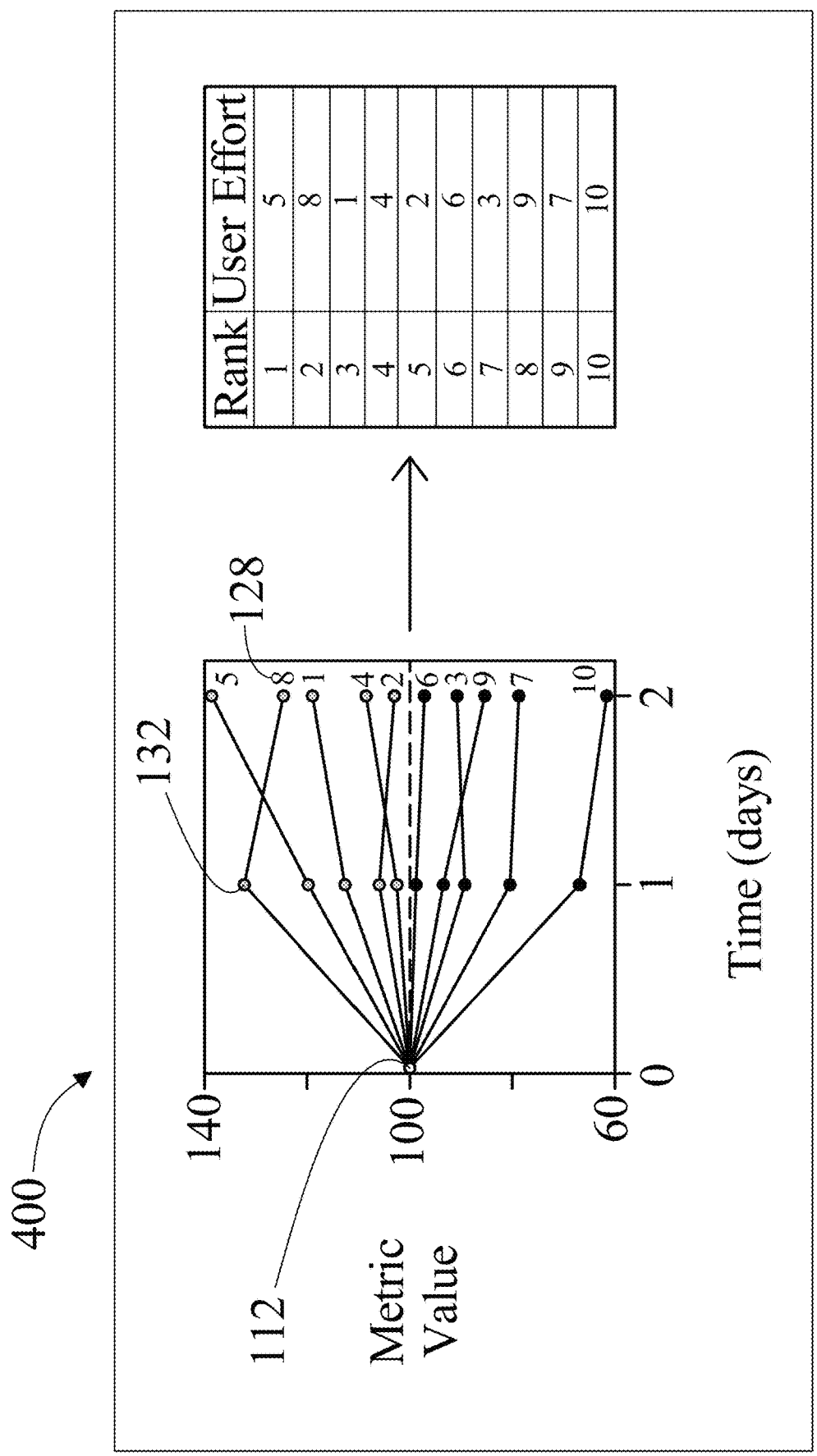
FIG. 4 is a diagrammatic representation of an output of simulated vitality metrics.

Referring now to FIG. 4, a non-limiting exemplary embodiment 400 of an output of a plurality of simulated metrics 132 generated by a simulation machine-learning process 136 with ranked user efforts 128 as a function of the simulated metrics 132 and a ranking machine-learning process 140 is illustrated. A vitality metric (white circle; at initial time ($T_0$)) may be used as an initial value for a simulation algorithm. Simulation machine-learning process 136 may then apply user efforts 128 to the vitality metric 112 which will result in traces (denoted by lines between points) that ultimately result in simulated metrics 132 at various time points after a vitality metric 112 (on the order of days as shown in FIG. 4). Simulation algorithm may use a threshold (denoted as a horizontal dashed line), wherein the threshold metric value is the current trajectory of the vitality metric 112. Such a threshold metric value may be used to determine which simulated metrics 132 have an increase in vitality metric (denoted as grey circles) and which decrease a vitality metric (denoted as black circles). User efforts 128 (ten shown; numbered as 1-10) that resulted in simulated metrics with, for instance and without limitation, increases in a vitality metric, may then be stored and/or retrieved alongside the simulated metric 132 data, wherein the user efforts 128 may be ranked using a ranking machine-learning process 140 and provided to a user to inform future user efforts. Persons skilled in the art may appreciate that a simulation algorithm may generate many orders of magnitude larger datasets of simulated metrics 132 than is illustrated in FIG. 4.

Referring back to FIG. 1, computing device 104 is configured to provide, to a user, a vitality metric 112 and at least a user effort 128 that resulted in a simulated metric 132. Computing device 104 may provide at least a vitality metric 112 and a user effort 128 via a user device. A user device may be a smartphone, laptop, tablet, or any other device with capabilities of a computing device as described herein. Computing device 104 may provide to a user a simulated metric 132. Computing device 104 may provide, display, or otherwise communicate the above using a graphical user interface (GUI), or any other interface suitable for displaying graphics, text, and the like. Persons skilled in the art, upon review of this disclosure in its entirety, will be aware of the various ways in which the data herein may be provided to a user, including what devices may be suitable as user devices for providing the data.

Continuing in reference to FIG. 1, computing device 104 providing to a user, a vitality metric 112 and a user effort 128 may include determining spatial data corresponding to a user and calculating, using a mapping algorithm, a path to a user effort location for the user to perform the user effort 128. As used in this disclosure, "spatial data" are coordinates that refer to a user's location on a map and an associated timestamp that places a user at a location at a specific time. Spatial data 144 may include information regarding a floor of a building, street address, or the like, and the times of being at each location, wherein the times and location may indicate a mode of transportation. Spatial data 144 may be global positioning system (GPS) coordinates, geographical coordinates such as longitude and latitude degrees, an address, or any other data identifiable as location data that may be used to navigate using a map. A "mapping algorithm" as used in this disclosure is an algorithm, or series of algorithms found in mapping software, or the like, that can be used to generate driving directions, walking directions, or the like, using spatial data 144. Mapping machine-learning process 148 may be a machine-learning process that can "call" or otherwise execute a commercial web-based mapping tool, application, and/or service such as, for instance and without limitation, GOOGLE MAPS, that is integrated into a user device for navigation purposes. In non-limiting illustrative examples, mapping machine-learning process 148 may iteratively determine outputs using the mapping tool as a function of updated user spatial data 144, among other inputs. A "path" as used in this disclosure is a navigation path that is provided via a map as directions to a location. A path 152 may include directions, such as walking directions and/or driving directions from a user's current location to a user effort 128 location as determined by the mapping machine-learning process 148. In non-limiting illustrative examples, a path 152 may include direction for a user to locate the nearest gym that has a stationary bike for a certain amount of time of biking exercise.

Continuing in reference to FIG. 1, ranked user efforts 128 from simulated metrics 132 may be provided to a user to be selected via a user interface, wherein selecting a user effort may include providing an instruction to perform the effort. An "instruction," as used in this disclosure, is an element of information provided to a user for performing a user effort 128. In non-limiting illustrative examples, an instruction may be to use a eat a meal with particular phytonutrients that are lacking, wherein the instruction is to go to a particular restaurant, cafeteria, dining hall, or the like, where a menu items can be found, and follow a path 152 to reach the particular location. Alternatively or additionally, a user may select a user effort 128 from a ranked queue of efforts to improve a vitality metric 112 to a degree determined in the simulated metric 132, wherein the effort is to seek mental health counseling. In such an example, an instruction may be a location to a mental health professional, a phone number to contact a mental health professional, among other instructions a user may follow to perform the user effort 128. Selection of a user effort 128 may be performed via a GUI, or other suitable user interface for selecting text, graphics, or the like. Persons skilled in the art upon review of the disclosure in its entirety will be aware the various ways in which user efforts may be provided to a user via a user device and selected using a user interface.

Figure 5:
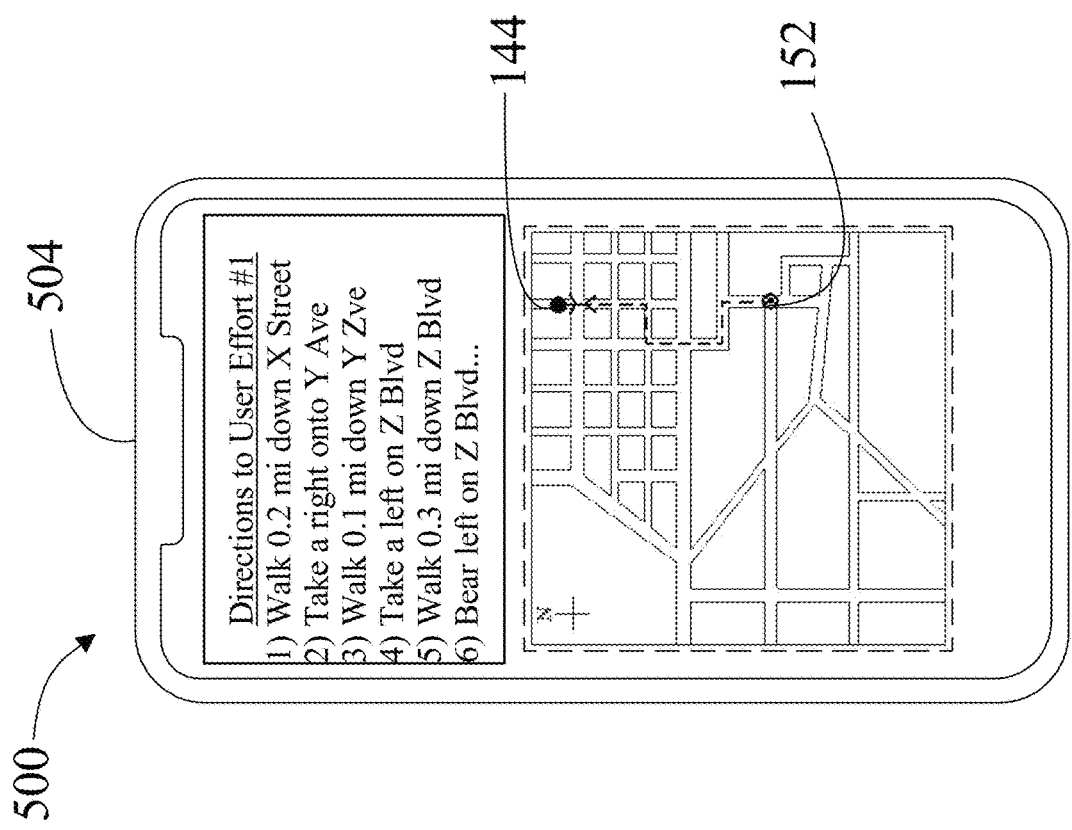
FIG. 5 is a diagrammatic representation of a user device displaying a path for a user effort.

Referring now to FIG. 5, a non-limiting exemplary embodiment 500 of a user device 504 providing a path 152 to a user effort 128 is illustrated. User device 504 may provide to a user a path 152 based on spatial data 144 that refers to a user effort 128 location and a user's current location. User device 504 may provide a path 152 via a mapping machine-learning process 148 used by the computing device 104. In non-limiting example embodiments, a user may select a user effort 128 location for a path to be determined.

Referring back to FIG. 1, computing device 104 may be configured to receive at least a user effort 128 from a user, generate a second vitality metric 112 as a function of at least a user effort 128 using the metric machine-learning model 116, wherein calculating a second vitality metric 112 may include determining how a user effort 128 has impacted a numerical parameter corresponding to a first vitality metric 112. Computing device 104 may use the metric machine-learning model 116 to generate a second vitality metric 112, wherein a second vitality metric 112 may be an updated vitality metric 112 that is determined with biotic extraction 108 data that is updated to reflect a user effort 128, as described above. Calculating a second vitality metric 112 may include using the trained model to recalculate the vitality metric 112 based on prior determinations corresponding to the magnitude of numerical impact a user effort 128 may have.

Continuing in reference to FIG. 1, computing device 104 may identify a numerical difference between a first vitality metric and a second vitality metric, wherein determining a numerical different includes determining how user efforts 128 impacted the metric. Computing device 104 may use any mathematical operation, for instance and without limitation subtraction, to determine a numerical difference between two or more vitality metrics 112. Computing device 104 may compare the sets of biotic extraction data and/or user efforts between the two or more vitality metrics to identify if the numerical difference in metric may be attributed to a user effort 128.

Figure 6:
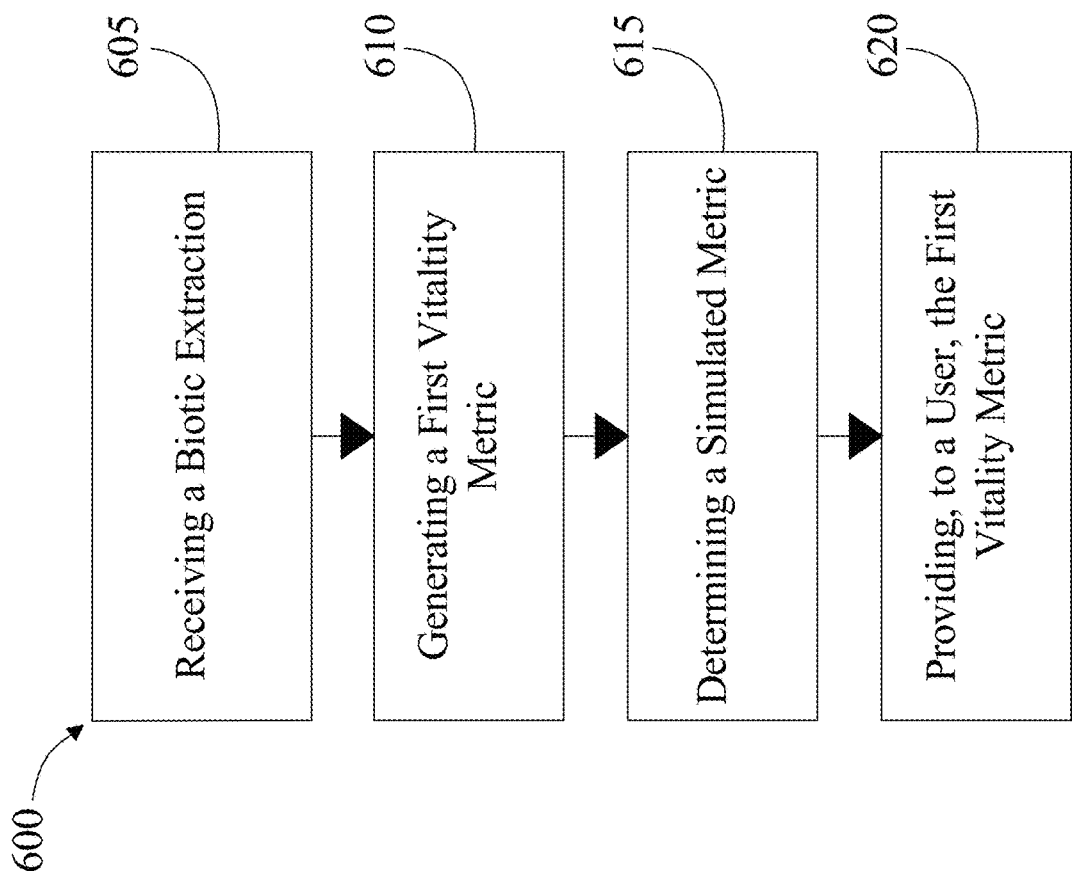
FIG. 6 is a flow diagram illustrating an exemplary method for simulating a vitality metric.

Referring now to FIG. 6, an exemplary embodiment of a method 600 of simulating a vitality metric is illustrated. At step 605, computing device 104 receives, from a user, a biotic extraction 108. Biotic extraction 108 may include data from a wearable device; this may be implemented, without limitation, as described above in reference to FIGS. 1-6.

With continued reference to FIG. 6, at step 610, computing device 104 generates a vitality metric 112 using a metric machine-learning model 116 and the biotic extraction 108, wherein generating a vitality metric 112 may include training a metric machine-learning model 116 with training data 120 corresponding to measuring biotic parameters present in the biotic extraction 108 data, and determining a metric that is a summation of all individual biotic parameters present in the biotic extraction 108 data. Generating a vitality metric 112 may include calculating a numerical metric for biotic parameters in the biotic extraction by using the metric machine-learning model 116. A vitality metric 112 may be determined as a function of at least a user effort 128, wherein a vitality metric 112 is provided periodically to a user as a function of the user efforts 128; this may be implemented, without limitation, as described above in reference to FIGS. 1-6.

With continued reference to FIG. 6, at step 615, computing device 104 determines a simulated metric 132, using a simulation machine-learning process 136 and a generated vitality metric 112 of a user, wherein determining a simulated metric 132 may include generating a simulation machine-learning process 136, wherein the simulation machine-learning process 136 perturbs a biotic parameter present in the vitality metric 112, wherein a biotic parameter is a variable element of data relating to an element present in the at least a user biotic extraction 108. Determining a simulated metric 132 of a user may include generating a simulated vitality metric, using a first vitality metric 112 of a user as an input and a simulation machine-learning process 136, wherein the simulation machine-learning process 136 generates a simulated metric 132 corresponding to a numerical output, wherein the simulated metric 132 is a vitality metric 112 after applying a user effort 128, and Providing, to a user, at least a simulated vitality metric as a function of a plurality of user efforts 128. Determining a simulated metric 132 may include identifying, as a function of the simulation machine-learning process 136 output, parameters that result in a simulated metric 132 that represent an improved vitality metric 112. Simulating a vitality metric 112 may include ranking, using a ranking machine-learning process 140, user efforts 128 as a function of the numerical change of the vitality metric 112. Ranked user efforts 128 from simulated metrics 132 are provided to a user to be selected via a user interface, wherein selecting a user effort may include providing an instruction to perform the effort; this may be implemented, without limitation, as described above in reference to FIGS. 1-6.

With continued reference to FIG. 6, at step 620, computing device 104 provides to a user, at least a simulated vitality metric 112 as a function of a plurality of user efforts 128. Providing, to a user, a vitality metric 112 and a user effort 128 may include determining spatial data 144 corresponding to a user, and calculating, using a mapping machine-learning process 148, a path 152 to a user effort 128 location for the user to perform the user effort 128. Computing device 104 may receive at least a user effort 128 from a user, generate a second vitality metric as a function of at least a user effort 128 using the metric machine-learning model 116, wherein calculating a second vitality metric may include determining how a user effort 128 has impacted a numerical parameter corresponding to a first vitality metric 112, and identify a numerical difference between a first vitality metric and a second vitality metric, wherein determining a numerical different includes determining how user efforts 128 impacted the metric; this may be implemented, without limitation, as described above in reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
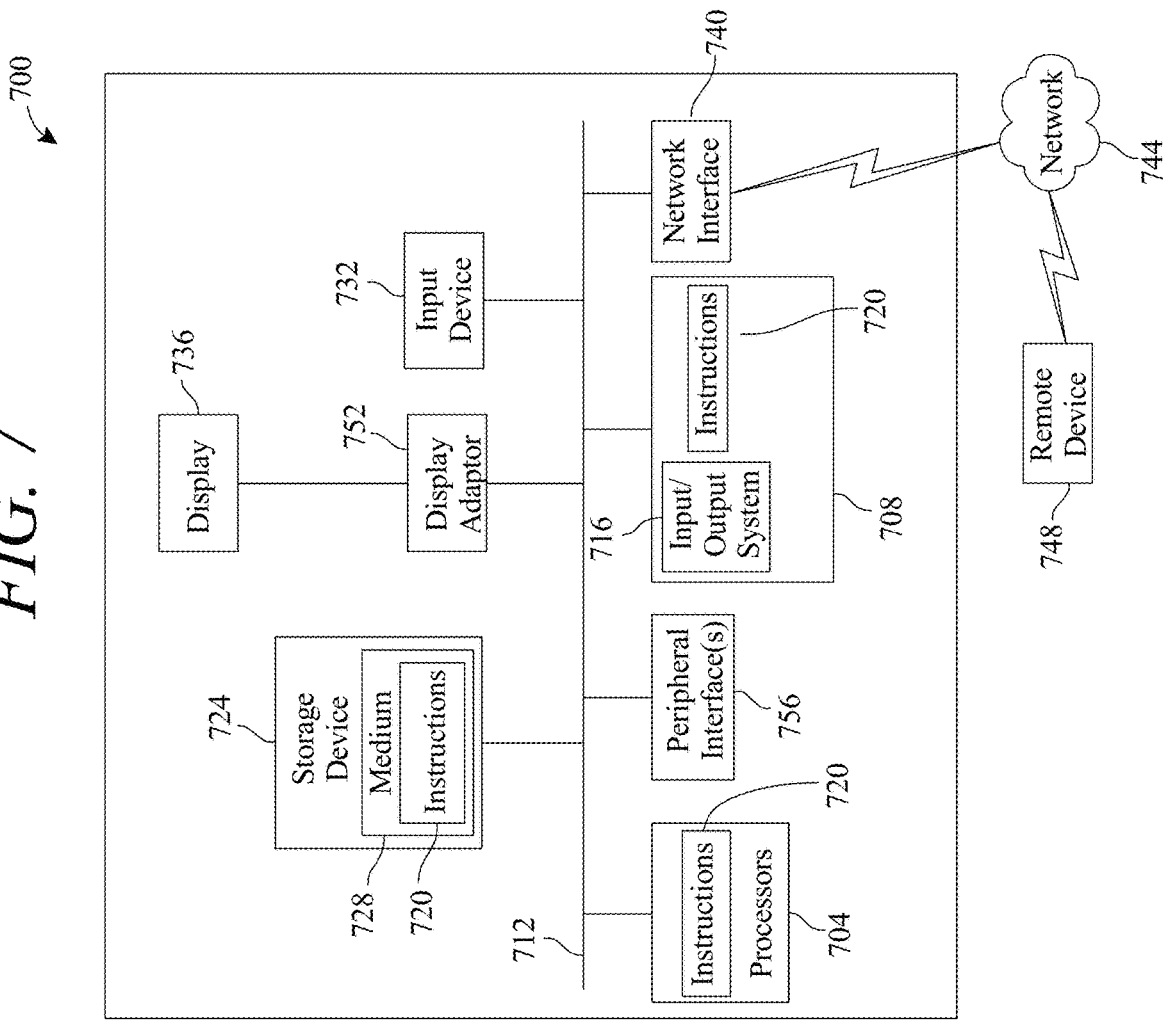
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for simulating a vitality metric, the system comprising a computing device, wherein the computing device is designed and configured to:
    retrieve a biotic extraction pertaining to a user;
    generate a first vitality metric using a metric machine-learning model and the biotic extraction, wherein generating the first vitality metric further comprises:
        training a metric machine-learning model with training data, the training data containing training data classifiers that classify biotic extraction data to subsets of users and the corresponding numerical values;
        generating the first vitality metric, the first vitality metric containing a summation of all individual biotic parameters associated with the biotic extraction data, as a function of the metric machine-learning model;
    determine a simulated metric as a function of the generated first vitality metric of a user,
        wherein determining the simulated metric further comprises:
            inputting, at a simulation machine-learning model, the first vitality metric;
            calculating an output for all values within a range of values corresponding to a parameter in the biotic extraction data as a function of the simulation machine-learning model;
            perturbing a biotic parameter present in the first vitality metric as a function of the simulation machine-learning model using a Monte Carlo algorithm, wherein perturbed value comprises a qualitative value, wherein the qualitative value comprises a discrete category; and
            determining, as a function of an output of the simulation-machine learning model, a simulated metric; and
    provide, to a user, the first vitality metric and at least a user effort that produces the simulated metric, wherein providing the first vitality metric and the at least a user effort further comprises:
        determining spatial data corresponding to the user; and
        calculating, using a mapping machine-learning process and the spatial data, a path to a location corresponding to the at least a user effort, wherein the path comprises directions to a facility that has exercise equipment for performing the at least a user effort.

2. The system of claim 1, wherein the biotic extraction further comprises data from a wearable device.

3. The system of claim 1, wherein generating the first vitality metric further comprises calculating a numerical metric for the biotic parameters using the metric machine-learning model.

4. The system of claim 1, wherein the first vitality metric is determined as a function of the at least a user effort.

5. The system of claim 1, wherein the first vitality metric is provided periodically to the user as a function of the at least a user effort.

6. The system of claim 1, wherein determining the simulated metric further comprises identifying a parameter that results in a simulated metric representing an improved first vitality metric.

7. The system of claim 1 further comprising ranking, using a ranking machine-learning process, the at least a user effort as a function of a numerical change of the first vitality metric.

8. The system of claim 7 further comprising:
    providing the at least a ranked user effort to the user via a user interface; and
    receiving, via the user interface, an instruction to perform the at least a user effort.

9. The system of claim 1, wherein the computing device is further configured to:
    receive an indication from a user that the at least a user effort has been performed;
    generate a second vitality metric as a function of the at least a user effort using the metric machine-learning model, wherein calculating the second vitality metric further comprises determining how the at least a user effort has impacted a numerical parameter corresponding to the first vitality metric; and
    identify a numerical difference between the first vitality metric and the second vitality metric, wherein determining the numerical difference includes determining how the at least a user effort impacted the second vitality metric.

10. A method for simulating a vitality metric, the method comprising:
    retrieving, by a computing device, a biotic extraction pertaining to a user;

generating, by the computing device, a first vitality metric using a metric machine-learning model and the biotic extraction, wherein generating the first vitality metric further comprises:
training a metric machine-learning model with training data, the training data containing training data classifiers that classify biotic extraction data to subsets of users and the corresponding numerical values; and
generating the first vitality metric, the first vitality metric containing a summation of all individual biotic parameters associated with the biotic extraction data, as a function of the metric machine-learning model;
determining, by the computing device, a simulated metric as a function of the generated first vitality metric of a user, wherein determining the simulated metric further comprises:
inputting, at a simulation machine-learning model, the first vitality metric;
perturbing a biotic parameter present in the first vitality metric as a function of the simulation machine-learning model using a Monte Carlo algorithm, wherein perturbed value comprises a qualitative value, wherein the qualitative value comprises a discrete category; and
determining, as a function of an output of the simulation-machine learning model, the simulated metric; and
providing, by the computing device, to a user, the first vitality metric and at least a user effort that produces the simulated metric, wherein providing the first vitality metric and the at least a user effort further comprises:
determining spatial data corresponding to the user, and calculating, using a mapping machine-learning process and the spatial data, a path to a location corresponding to the at least a user effort, wherein the path comprises directions to a facility that has exercise equipment for performing the at least a user effort.

11. The method of claim 10, wherein the biotic extraction further comprises data from a wearable device.

12. The method of claim 10, wherein generating the first vitality metric further comprises calculating a numerical metric for the biotic parameters using the metric machine-learning model.

13. The method of claim 10, wherein the first vitality metric is determined as a function of the at least a user effort.

14. The method of claim 10, wherein the first vitality metric is provided periodically to the user as a function of the at least a user effort.

15. The method of claim 10, wherein determining the simulated metric further comprises identifying a parameter that results in a simulated metric representing an improved first vitality metric.

16. The method of claim 10 further comprising ranking, using a ranking machine-learning process, the at least a user effort as a function of a numerical change of the first vitality metric.

17. The method of claim 16 further comprising:
providing the at least a ranked user effort to the user via a user interface; and
receiving, via the user interface, an instruction to perform the at least a user effort.

18. The method of claim 10 further comprising:
receiving an indication from a user that the at least a user effort has been performed;
generating a second vitality metric as a function of the at least a user effort using the metric machine-learning model, wherein calculating the second vitality metric further comprises determining how the at least a user effort has impacted a numerical parameter corresponding to the first vitality metric; and
identify a numerical difference between the first vitality metric and the second vitality metric, wherein determining the numerical difference includes determining how the at least a user effort impacted the second vitality metric.

* * * * *